United States Patent [19]

Retzer

[11] 3,992,150
[45] Nov. 16, 1976

[54] METHOD AND EQUIPMENT FOR SPEEDY PREPARATION OF TEST LIQUIDS

[75] Inventor: Erich Retzer, Maisach, Germany

[73] Assignee: Compur-Werk Gesellschaft mit beschraenkter Haftung & Co., Munich, Germany

[22] Filed: Apr. 28, 1975

[21] Appl. No.: 572,222

[30] Foreign Application Priority Data

May 8, 1974 Germany............................ 2422260

[52] U.S. Cl. ............................ 23/230 R; 23/230 B; 23/253 R; 23/259; 73/425.4 P; 128/2 F; 128/DIG. 5; 356/246

[51] Int. Cl.² ..................... A61B 10/00; B01L 3/02; G01N 1/10; G01N 33/16

[58] Field of Search .......... 23/230 R, 230 B, 253 R, 23/259, 292; 73/425.4 P; 356/246 (U.S. only); 128/2 F, 2 G, DIG. 5

[56] References Cited
UNITED STATES PATENTS

| 3,475,127 | 10/1969 | Gilford............................. 23/230 R |
| 3,506,367 | 4/1970 | Ross et al. .......................... 356/246 |
| 3,518,804 | 7/1970 | Gerarde............................. 23/259 X |
| 3,603,156 | 9/1971 | Konkol........................... 73/425.4 P |
| 3,676,076 | 7/1972 | Grady................................... 23/292 |
| 3,682,597 | 8/1972 | Husch.................................. 23/259 |
| 3,811,326 | 5/1974 | Sokol............................... 23/292 X |
| 3,834,876 | 9/1974 | Kormendy et al. .................. 23/259 |

*Primary Examiner*—Joseph Scovronek
*Attorney, Agent, or Firm*—Stonebraker, Shepard & Stephens

[57] ABSTRACT

A cuvet is prepared for test analysis of a substance by placing a predetermined volume of a reagent liquid in a cuvet and then using a pipette or capillary tube for taking up a predetermined volume of the test substance by capillary action. Then the charged capillary tube is placed in the cuvet in the reagent liquid to permit the test substance to flow into the reagent liquid, and the substance is mixed with the reagent liquid in the cuvet so that the substance has a precise and predetermined ratio to the reagent liquid for speedily and accurately preparing the cuvet for a test analysis. A convenient kit is provided, containing a plurality of cuvets already charged with a measured quantity of a reagent liquid, and a plurality of capillary pipettes for use in adding measured quantities of some other liquid (e.g., blood) to the reagent liquid in a cuvet.

10 Claims, 7 Drawing Figures

U.S. Patent     Nov. 16, 1976     3,992,150
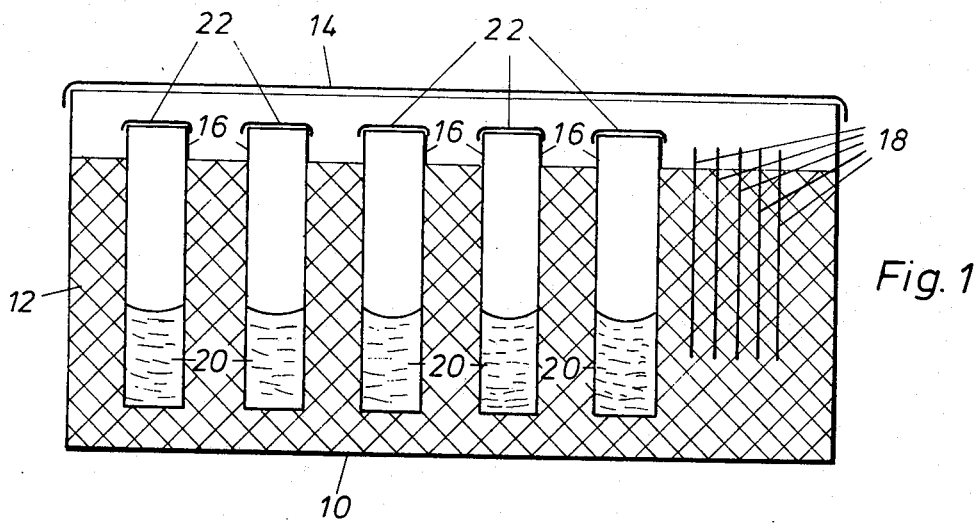
Fig. 1
Fig. 2
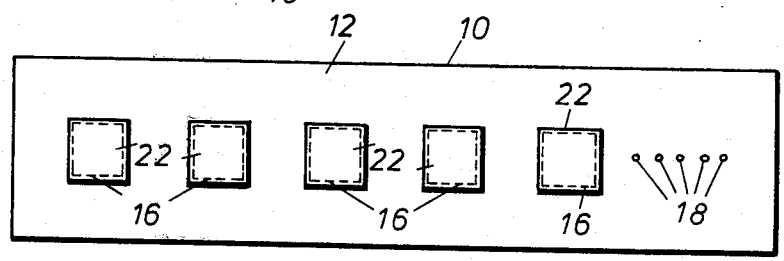
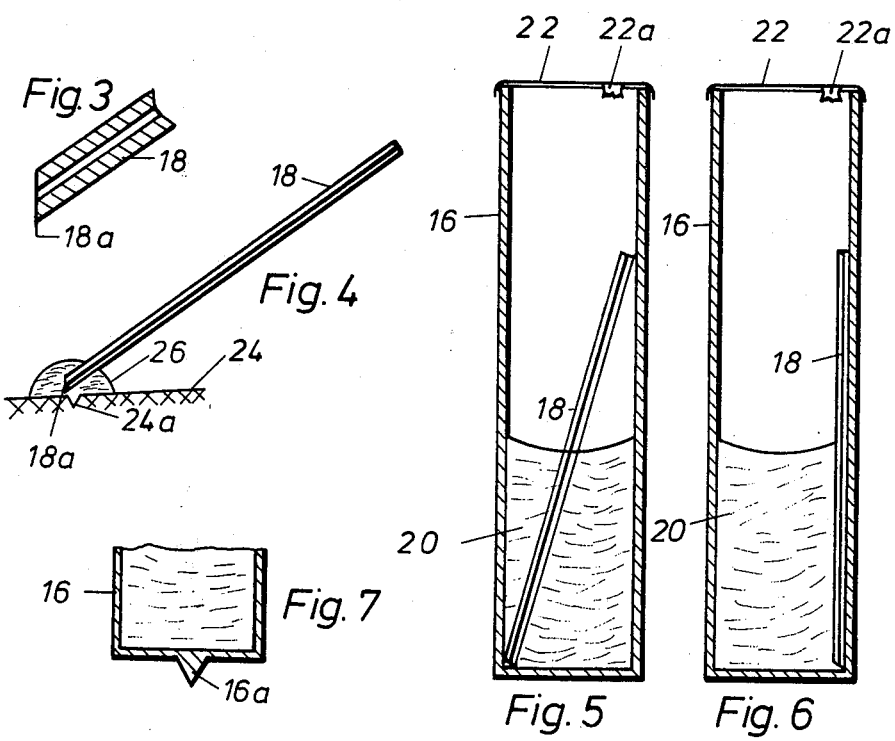
Fig. 3
Fig. 4
Fig. 5
Fig. 6
Fig. 7

METHOD AND EQUIPMENT FOR SPEEDY PREPARATION OF TEST LIQUIDS

BACKGROUND OF THE INVENTION

A generally known procedure for photometric analysis of a substance uses a container called a cuvet made to have predetermined optical properties. A measured quantity of a reagent liquid is placed in the cuvet, and a precisely measured amount of the test substance is added to and mixed with the reagent liquid so that the test substance and the reagent liquid are exactly in a predetermined ratio to insure accuracy of the test. Then the cuvet is mounted in an analyzing appliance such as a photometer where light is directed through the cuvet and the reagent liquid containing the test substance for measuring the light permeability of the contents of the cuvet to analyze a property of the test substance. Cuvets are made in different sizes and of different materials, reagent liquids vary for different tests to be made, and different ratios of test substances to reagent liquids are used, depending on the materials involved. Photometric light transmittance tests can be made with ultra-violet or visible light, and measurement of light scattering and other optical effects can also be made by using cuvets.

Some photometric tests using cuvets are made for medical purposes, and one such test involves measuring the hemoglobin in human blood. Suitable reagent liquids and general test procedures are well known for measuring hemoglobin in the blood and for other medical and non-medical tests using cuvets.

The invention involves recognition of ways that prior art methods of preparing cuvets for test analyses are cumbersome, slow, and lead to inaccuracies unless great care is taken in accurately measuring the reagent liquid and the test substance to achieve the precise ratio desired between these materials. Especially for medical tests, which often have to be made speedily because a patient's condition requires prompt action after an accident or before some urgent operation, speedy and accurate cuvet preparation is highly desirable. The urgency in preparing a cuvet quickly during a medical emergency can easily lead to inaccuracy.

The invention also involves recognition of a way that a cuvet can be prepared speedily and easily with high and reliable accuracy using simple and convenient materials. The invention aims at speed and accuracy in cuvet preparation using relatively inexpensive materials.

SUMMARY OF THE INVENTION

The inventive cuvet preparation method uses a cuvet, a reagent liquid, and a pipette or capillary tube sized for taking up a predetermined volume of a test substance by capillary action. First a predetermined volume of the reagent liquid is placed in the cuvet and preferably hermetically sealed. Then the end of the pipette is inserted in the test substance to charge the pipette with a predetermined volume of the test substance by capillary action, which happens very quickly. Preferably, the charged pipette is then used to pierce through the seal over the cuvet and the charged capillary tube is inserted in the reagent liquid in the cuvet to permit the test substance to flow into the reagent liquid. The test substance and reagent liquid are mixed together in the cuvet with the test substance having a precise and predetermined volumetric ratio to the reagent liquid, and the cuvet is then directly ready for test analysis.

Preferably, a small container stores a number of cuvets and a corresponding number of capillary tubes or pipettes, and the capillary tubes preferably have beveled cutting ends that can be used to make an incision in a human body to secure the test substance, and are also useful for piercing the frangible or penetrable sealing membrane at the top of the cuvet. Alternatively, the cuvet itself can be made with a cutting edge that can be used to make an incision in a human body.

BRIEF DESCRIPTION OF THE DRAWINGS

FIG. 1 is a vertical longitudinal cross-sectional view of a container equipped with cuvets and pipettes according to the invention;

FIG. 2 is a plan view of the container of FIG. 1 with the cover removed;

FIG. 3 is an enlarged fragmentary cross-sectional view of the cutting end of a pipette;

FIG. 4 is an enlarged partially sectioned view of a pipette being charged with human blood;

FIGS. 5 and 6 are enlarged cross-sectional views of a cuvet and a pipette in two different stages of operation; and FIG. 7 is an enlarged, fragmentary cross-sectional view of the bottom of a cuvet having a cutting edge or point.

DETAILED DESCRIPTION OF THE INVENTION

The equipment used in practicing the invention will first be described, and then operations involving the invention will be explained. The invention is generally applicable to cuvet preparation for any purpose, but is especially convenient for medical tests, and is explained relative to medical testing.

Although the invention can be practiced with a single cuvet and a single capillary tube or pipette, it is preferred that several cuvets 16 be stored in a container 10 having a filler mass 12 such as a molded foamed plastic or rubber material having cavities for receiving each of the cuvets 16. The filler mass 12 preferably has smaller reception openings for capillary tubes or pipettes 18, but the tubes 18 can also be pushed into the filler mass 12 without requiring reception openings. Preferably an equal number of the cuvets 16 and the tubes 18 are stored in each container 10 in sterile condition and protected by a cover 14 to form a kit or set ready for several cuvet preparations.

The cuvets 16 are shown in approximately actual size in FIGS. 1 and 2, although the cuvets 16 can be made in many different sizes. The cuvets 16 are preferably square in horizontal cross section and are formed of a clearly transparent material, such as a thin clear plastics material. The cuvets 16 can also be formed of glass or crystalline material that is generally clear and transparent. Each of the cuvets 16 is filled with a predetermined equal volumetric quantity of a desired reagent liquid material 20. Then the top opening of each of the cuvets 16 is hermetically sealed with a seal 22 preferably formed of a material which is frangible or penetrable, such as a thin adhesive foil, to preserve the exact amount of the reagent liquid 20. For cuvets having a volumetric capacity of about 4 cubic centimeters, a reagent liquid charge of about 1.5 cubic centimeters is preferred.

The capillary tubes 18, also referred to as pipettes, are preferably made of clear glass in a generally known way. The tubes 18 can be made in different sizes, and the size illustrated in the drawings has an outside diameter of about 1 mm., an inside diameter of about 0.5 mm., and a length of about 30 mm. The tubes 18 can be made by generally known mass-production methods with a very high degree of dimensional accuracy for any desired parameters. The tubes 18 are preferably dipped in a moistening liquid that insures that the molecular forces between a test liquid and the inside wall of the tubes 18 produce a capillary effect drawing the test liquid up into the tubes 18. This phenomenon is generally known and varies with the inside diameter of the capillary in the tube 18 and the specific gravity of the liquid entering the capillary. The rising of a liquid up into the capillary of a tube 18 is automatic and fast (occurring within a few seconds), and if the tubes 18 are dimensionally accurate and constant, as they can be with mass production, each of the tubes 18 will take up an exact and constant volumetric charge of a particular substance or liquid to be measured. Thus, the capillary tubes 18 afford speedy and highly accurate measuring and retaining devices for small quantities of any particular substance to be tested.

One open end of each tube 18 is preferably formed as a knife edge 18a by cutting at a bevel angle oblique to the axis of the tube, as best shown in the enlarged view of FIG. 3. The edge 18a can then be used to cut or puncture a small incision in human skin. Moreover, the cutting edge 18a is useful for piercing through the closure foil 22 sealing the cuvets 16 so the tube 18 can be inserted into the cuvet 16. Alternatively, a cutting edge or point 16a can be formed on the bottom of each cuvet 16, and can be used to cut or puncture an incision through human skin. The cutting edge 16a can be formed elsewhere on each cuvet 16, such as along a lower edge of the cuvet.

The operation of the invention will be described for the preparation of a cuvet for a test of hemoglobin in the blood, although it is understood that the inventive method and equipment applies to cuvet preparation for other purposes.

First the container 10 is prepared with several sterile cuvets and pipettes or capillary tubes as previously explained, with each cuvet 16 containing an accurately measured volume of a suitable reagent liquid 20. The user then takes a capillary tube 18 from the container 10 and with the cutting end 18a makes an incision or puncture through the human skin at the part of the body from which a blood sample is to be taken. FIG. 4 shows on a somewhat larger scale the way the cutting edge 18a has made an incision opening 24a in the skin 24 so that a drop of blood 26 comes out of the opening 24a. The end 18a of the capillary tube 18 is then inserted in the drop of blood 26 that comes from the incision 24a, and the blood rises within fractions of a second into the capillary of tube 18. The volumetric amount of blood rising into the capillary is accurately predetermined by the diameter of the capillary and is secured and retained in the capillary tube 18 very quickly. The user then removes a cuvet 16 from the container 10, and with the cutting edge 18a of the charged capillary tube 18, pierces or punctures through the foil seal 22 to make an opening 22a through which the capillary tube 18 is inserted into the interior of the cuvet 16, as shown in FIG. 5.

The charge of blood within the capillary of the tube 18 then flows out of the capillary and into the reagent liquid 20 and mixes with the reagent liquid. The user preferably shakes the cuvet 16 with the capillary tube 18 inside the cuvet to accelerate the mixing of the blood and the reagent liquid 20. Such shaking also moves the empty capillary tube 18 into one of the vertical corners of the cuvet where it is held in place by capillary action, as best shown in FIG. 6. This gets the capillary tube 18 out of the way for photometric testing of the blood and the reagent liquid 20 in the cuvet.

Since the volumetric quantity of reagent liquid is predetermined and constant for each cuvet 16, and since the volumetric amount of blood secured by each of the capillary tubes 18 is also constant and predetermined, exactly the same constant mixture ratio between blood and reagent liquid is achieved for each test after the capillary tube 18 is inserted into the cuvet 16 and the blood is fully mixed together with the reagent liquid. The cuvet 16 prepared according to the invention is then mounted in a suitable measuring appliance, such as a photometer, and known test procedures are used to measure the degree of light permeability of the cuvet contents to determine the amount of hemoglobin in the blood.

Preferably all the cuvets and capillary tubes in a single container 10 are used for the same sort of test, such as the hemoglobin test described above. This allows constant and identical charges of the reagent liquid 20 to be placed in each of the cuvets 16 to secure highly accurate results by using capillary tubes having constant and uniform parameters. For different tests requiring different parameters of cuvets and capillary tubes or different reagent liquids, other sets can be made and can be distinguished by color coding or labeling the containers 10, the covers 14, the seals 22, or the cuvets 16. Where the substance to be tested is not from the human body, no cutting edges 18a or 16a are required, and if the substance to be tested is stored in a container, an appropriate amount of the substance can be taken up quickly merely by inserting one end of a capillary tube 18 into the substance.

Those skilled in the art will appreciate the many parameters and materials that can be used in applying the invention to different tests, and will appreciate the ease and accuracy obtainable. Suitable materials, parameters, and mixture ratios can readily be determined and easily applied for many test preparations according to the invention.

The container 10 and its enclosed cuvets 16 and pipettes 18 constitute a very convenient and compact kit which may be easily carried in a doctor's bag or in an ambulance, or placed in convenient locations in the emergency department of a hospital.

What is claimed is:
1. A method of preparing a test liquid for analysis of a liquid substance, said method using said liquid substance, a reagent liquid, a cuvet having predetermined transparent characteristics suitable for optical measuring of said test liquid in said cuvet, and a capillary tube sized for taking up a predetermined, full charge volume of said liquid substance by capillary action, said method comprising the steps of:
   a. placing a predetermined volume of said reagent liquid in said cuvet;
   b. placing a seal member over the opening to said cuvet;
   c. inserting an end of said capillary tube in said liquid substance to fully charge said capillary tube with said predetermined volume of said liquid substance by capillary action alone;

d. breaking an opening in said seal member;
e. thrusting said charged capillary tube through said opening in said seal member and into said reagent liquid in said cuvet to permit said liquid substance to flow into said reagent liquid;
f. mixing said liquid substance flowing out of said capillary tube with said reagent liquid in said cuvet to form said test liquid having a precise and predetermined volumetric ratio of said liquid substance to said reagent liquid; and
g. making said test analysis of said test liquid in said cuvet without removing said capillary tube from said cuvet.

2. The method of claim 1 including making an incision in a human body and inserting said end of said capillary tube in said liquid substance coming from said incision to fully charge said capillary tube.

3. The method of claim 2 wherein said capillary tube has a bevelled cutting end and including making said incision with said cutting end of said capillary tube.

4. The method of claim 2 wherein said cuvet has a cutting edge and including making said incision with said cutting edge of said cuvet.

5. The method of claim 1 wherein said liquid substance is in a storage container and including inserting said end of said capillary tube in said substance in said storage container to fully charge said capillary tube.

6. The method of claim 1 wherein said cuvet is rectangular in horizontal cross section and including shaking said cuvet to move said capillary tube into a vertical corner of said cuvet where said capillary tube is retained by capillary action during said test analysis.

7. A portable kit for preparing a plurality of test liquids for the same predetermined test analysis, said kit comprising:
a. a closable container;
b. a plurality of identical cuvets having predetermined transparent characteristics suitable for optical measuring of said test liquid in said cuvet;
c. a predetermined volume of a reagent liquid in each of said cuvets;
d. a seal member hermetically sealing said reagent liquid volume in each of said cuvets;
e. said container having a plurality of cuvet storage recesses;
f. said sealed cuvets being lodged respectively in said storage recesses;
g. a plurality of capillary tubes sized for taking up a predetermined, full charge volume of a liquid substance by capillary action;
h. means for holding said capillary tubes in said container;
i. said seal members being breakable to provide an opening into said cuvets; and
j. said capillary tubes being sized for insertion respectively into said cuvets through said openings in said seal members for mixing said predetermined volume of said liquid substance with said predetermined volume of said reagent liquid in a precise and predetermined volumetric ratio to form said test liquid ready for said test analysis.

8. The kit of claim 7 wherein each of said capillary tubes has a bevelled cutting edge for making an incision in a human body.

9. The kit of claim 7 wherein each of said cuvets has a cutting edge for making an incision in a human body.

10. The kit of claim 7 wherein each of said cuvets is rectangular in horizontal cross section so each of said capillary tubes is retained by capillary action in a vertical corner of said cuvets during said test analysis.

* * * * *